(12) United States Patent
Vanderveen et al.

(10) Patent No.: US 11,517,671 B2
(45) Date of Patent: Dec. 6, 2022

(54) SYSTEMS AND METHODS FOR CONTROLLING AN INFUSION PUMP

(71) Applicant: CareFusion 303, Inc., San Diego, CA (US)

(72) Inventors: Timothy W. Vanderveen, Poway, CA (US); Robert Dwaine Butterfield, Poway, CA (US)

(73) Assignee: CAREFUSION 303, INC., San Diego, CA (US)

( * ) Notice: Subject to any disclaimer, the term of this patent is extended or adjusted under 35 U.S.C. 154(b) by 539 days.

(21) Appl. No.: 16/661,467

(22) Filed: Oct. 23, 2019

(65) Prior Publication Data
US 2020/0054829 A1 Feb. 20, 2020

Related U.S. Application Data

(63) Continuation of application No. 15/289,075, filed on Oct. 7, 2016, now Pat. No. 10,485,926.

(51) Int. Cl.
*A61M 5/172* (2006.01)
*A61M 5/168* (2006.01)
(Continued)

(52) U.S. Cl.
CPC ............ *A61M 5/172* (2013.01); *A61M 5/142* (2013.01); *A61M 5/1407* (2013.01);
(Continued)

(58) Field of Classification Search
CPC ................ A61M 5/172; A61M 5/1407; A61M 5/16854; A61M 5/14228; A61M 5/142
See application file for complete search history.

(56) References Cited

U.S. PATENT DOCUMENTS 4,096,385 A 6/1978 Marett
4,533,347 A 8/1985 Deckert
(Continued)

FOREIGN PATENT DOCUMENTS

CN 2098293 U 3/1992
CN 1225038 A 8/1999
(Continued)

OTHER PUBLICATIONS

Chinese Office Action for Application No. 201780075566.2, dated Jan. 27, 2022, 8 pages including translation.
(Continued)

*Primary Examiner* — Nathan R Price
*Assistant Examiner* — Melissa A Snyder
(74) *Attorney, Agent, or Firm* — Morgan, Lewis & Bockius LLP (57) ABSTRACT

Systems and methods for determining the position of a fluid within a fluid source and infusion line coupled to an infusion flow control device are described herein. An exemplary system and method includes sampling fluid pressure upstream of an infusion pump, and calculating fluid pressure slope profiles. By sampling fluid pressure upstream of an infusion pump at discrete intervals and monitoring fluid pressure slope profiles, conditions of fluid flow, including unintentional fluid flow through an infusion line or a defective check valve in an infusion line, are detected, and fluid flow through an infusion pump is controlled.

20 Claims, 7 Drawing Sheets

(51) Int. Cl.
*A61M 5/142* (2006.01)
*A61M 5/14* (2006.01)

(52) U.S. Cl.
CPC .... *A61M 5/14228* (2013.01); *A61M 5/16854* (2013.01); *A61M 5/1414* (2013.01); *A61M 5/16818* (2013.01); *A61M 5/16827* (2013.01); *A61M 2005/16872* (2013.01); *A61M 2205/3334* (2013.01); *A61M 2205/3337* (2013.01); *A61M 2205/3351* (2013.01); *A61M 2205/3355* (2013.01)

(56) References Cited

U.S. PATENT DOCUMENTS

| | | | |
|---|---|---|---|
| 4,882,575 | A | 11/1989 | Kawahara |
| 5,096,385 | A * | 3/1992 | Georgi .............. A61M 5/16859 417/18 |
| 5,439,355 | A | 8/1995 | Jimison et al. |
| 5,695,473 | A | 12/1997 | Olsen |
| 5,951,510 | A | 9/1999 | Barak |
| 6,368,314 | B1 | 4/2002 | Kipfer et al. |
| 7,206,715 | B2 | 4/2007 | Vanderveen et al. |
| 2003/0078547 | A1 | 4/2003 | Shekalim |
| 2005/0107923 | A1 | 5/2005 | Vanderveen |
| 2007/0270782 | A1 | 11/2007 | Miesel et al. |
| 2010/0114027 | A1 | 5/2010 | Jacobson et al. |
| 2014/0221965 | A1 | 8/2014 | Regittnig et al. |
| 2014/0236119 | A1 | 8/2014 | Tsoukalis |
| 2015/0133889 | A1 | 5/2015 | Campagnolo et al. |
| 2015/0198501 | A1 | 7/2015 | Rule et al. |

FOREIGN PATENT DOCUMENTS

| | | |
|---|---|---|
| CN | 1688353 A | 10/2005 |
| CN | 1942210 A | 4/2007 |
| CN | 102100936 A | 6/2011 |
| CN | 102143775 A | 8/2011 |
| CN | 102196833 A | 9/2011 |
| CN | 202168979 U | 3/2012 |
| CN | 202777253 U | 3/2013 |
| CN | 104507516 A | 4/2015 |
| CN | 104815368 A | 8/2015 |
| CN | 204582137 U | 8/2015 |
| CN | 105142697 A | 12/2015 |
| EP | 1699509 A1 | 9/2006 |
| EP | 2305334 A2 | 4/2011 |
| WO | WO-9903518 A1 | 1/1999 |
| WO | WO-2016147699 A1 | 9/2016 |

OTHER PUBLICATIONS

Chinese Office Action for Application No. 201780075566.2, dated Dec. 31, 2020, 13 pages including machine translation.
European Office Action for Application No. 17778121.8, dated Aug. 6, 2020, 6 pages.
International Preliminary Report on Patentability for Application No. PCT/US2017/052784, dated Jan. 22, 2019, 24 pages.
Written Opinion of the International Preliminary Examining Authority for PCT Application No. PCT/US2017/052784, dated Aug. 30, 2018, 10 pages.
International Search Report and Written Opinion for Application No. PCT/US2017/052784, dated Dec. 1, 2017, 17 pages.
Australian Office Action for Application No. 2017340377, dated Sep. 9, 2021, 2 pages.
Chinese Office Action for Application No. 201780075566.2, dated Jul. 1, 2021, 18 pages including translation.
Chinese Office Action for Application No. 201780075566.2, dated Aug. 2, 2022, 13 pages including translation.

* cited by examiner

SYSTEMS AND METHODS FOR CONTROLLING AN INFUSION PUMP

CROSS REFERENCE TO RELATED APPLICATIONS

This application is a continuation application of U.S. application Ser. No. 15/289,075, entitled "SYSTEMS AND METHODS FOR CONTROLLING AN INFUSION PUMP," filed on Oct. 7, 2016, now U.S. Pat. No. 10,485,926, which issued on Nov. 26, 2019, the entirety of which is incorporated herein by reference.

BACKGROUND

Infusion of therapeutic fluids to treat patients is commonly used in hospitals and other medical care settings. Some infusions are carried out by hanging a bag or container of a fluid source on a pole above the patient so that fluid flows under the force of gravity through a length of tubing and into the vessel of a patient, and can be regulated by a user-controllable flow restrictor. In other instances, the flow of fluid into the patient is under the control of a programmed infusion pump located in the fluid pathway. The infusion pump is located in the fluid pathway such that a portion the container and infusion line is positioned above, or upstream, of the infusion pump.

Infusion pumps are 'displacement regulation' devices which permit precise control of the flow of a supply fluid, such as a medication, into the patient. For example, using an infusion pump, relatively precise amounts of fluid are infused at one or more specified flow rate. Moreover, the infusion pump may be programmed to change the rate of fluid flow during the infusion. This capability is useful where a primary fluid source, containing a first supply fluid, and a secondary fluid source, containing a second supply fluid, is coupled to the infusion pump. The infusion pump may be programmed to direct fluid to the patient at an initial rate when the second fluid is flowing to the pump, and then alter operation to direct fluid to the patient at a different rate when the second fluid is nearly empty and the first fluid begins to flow toward the pump.

SUMMARY

By determining fluid pressure slope profiles of a supply fluid directed by an infusion pump, the position of a fluid within a fluid source and an infusion line can be determined to automate the control of fluid flow through the infusion pump and to detect conditions of the fluid flow. Conditions of the fluid flow can include, unintentional fluid flow or a defective valve in an infusion line.

The present disclosure generally relates to systems and methods for determining the position of a fluid, and rate of change of the fluid position, within a fluid source and infusion line coupled to an infusion flow control device. More specifically, the present invention relates to systems and methods for determining supply fluid pressure slope profiles to detect conditions of the fluid flow, including unintentional fluid flow through an infusion line or a defective valve in an infusion line, and to automate the control of fluid flow through an infusion pump. Using supply fluid pressure slope profiles, the system may provide a local or remote audible and/or visual alert to a caregiver administering or monitoring the infusion and may initiate changes to the flow of fluid. For example, the system may change to an alternate flow rate, stop infusion, or provide a controlled flush to ensure timely delivery of a fluid contained in the infusion line.

Under certain circumstances, a malfunction causes a fluid to be directed from a fluid source at an unintended flow rate. For example, an infusion pump may experience a malfunction preventing control of the fluid flow rate, debris may be located within the tubing, or the tubing may have a leak. Under such circumstances, the fluid may be directed out of the fluid source and infusion line by the force of gravity. In some instances, the fluid is infused into the patient or directed into the environment. If a caregiver or other person is not monitoring the infusion process, the unintentional fluid flow may not be detected until the patient is harmed or medication is lost.

In some instances, a "primary" fluid source and a "secondary" fluid source are coupled to an infusion line (e.g., supply tubing) upstream of an infusion pump. The term "upstream" may refer to a portion of the infusion system that can include one or more fluid source, valve, infusion line, or other components that are coupled to a fluid intake of an infusion pump. The term "downstream" may refer to a portion of the infusion line system that can include an infusion line or other components extending from a fluid output of an infusion pump to a patient. To automate the transition of flow from a secondary fluid source to a primary fluid source when the secondary fluid is completed, a one-way check valve is inserted in the infusion line. The one-way check valve is inserted in the infusion line extending from the primary fluid source to the infusion pump ("primary line"), and the infusion line coupled to a secondary fluid source ("secondary line") is coupled to a port in the primary line between the check valve and the infusion pump. To fill, or "prime," the secondary line, the secondary fluid source container is lowered below the primary fluid source container. After the secondary line is filled with the primary fluid, the primary and secondary fluid source containers are secured so that the primary fluid source container is below the secondary fluid source container, typically, for example, about nine inches. The secondary fluid enters the primary line through the port between the check valve and the infusion pump. Fluid pressure exerted against the check valve by the secondary fluid prevents flow of the primary fluid toward the infusion pump. When the secondary fluid level is reduced to a level near the top of the fluid in the primary container, the pressure against the check valve reduces and the check valve permits the primary fluid to once again flow into the infusion line below the check valve.

Under certain circumstances, a malfunctioning or defective check valve will fail to obstruct the primary line when a secondary fluid source is coupled to the primary line between the check valve and the infusion pump. The defective check valve permits secondary fluid to flow past the check valve into the primary line and primary fluid source container until equilibrium is reached between the primary and secondary fluid. In some circumstances, the defective check valve permits the entirety of the secondary fluid to flow into the primary line and primary container, resulting in mixture of primary fluid and secondary fluid having an unknown concentration. The secondary fluid continues to flow into the primary line until equilibrium is reached when the secondary fluid level is reduced to a level near that of the top of the primary fluid in the primary fluid source container. After equilibrium is reached, simultaneous delivery of the primary and secondary fluid, and/or the mixture of primary and secondary fluid to the infusion pump, can occur.

Under certain circumstances, where infusion includes a primary fluid source and a secondary fluid source, the desired rate of secondary fluid flow is different from the desired rate of primary fluid flow. Accordingly, a caregiver must program the infusion pump with information that may include the volume of fluid in the secondary container, the total volume-to-be-infused, the rate of secondary fluid flow, or the secondary fluid infusion time. After the infusion pump infuses the secondary fluid for the preset volume, rate, or time, the infusion pump will change to the rate of primary fluid flow. However, frequent errors due to incorrect estimation of container volume or inaccurate setting of the secondary volume-to-be-infused renders this method unreliable, requiring frequent monitoring by a caregiver to ensure that the intended fluid is being directed at the desired rate, and that complete delivery of the intended fluid is achieved.

An aspect of the present disclosure provides, a method of detecting unintentional fluid flow through an infusion line, the method comprising: sampling fluid pressure within the infusion line upstream of the infusion pump; calculating an actual fluid pressure slope profile, the fluid pressure slope profile being a change in pressure over discrete intervals; comparing the actual fluid pressure slope profile with an expected fluid pressure slope profile; and altering operation of the infusion pump if the change in pressure of the actual fluid pressure slope profile varies from a coincident change in pressure of an expected fluid pressure slope profile by a predetermined threshold.

In some aspects of the present disclosure, altering operation of the infusion pump includes activating an alarm. In some implementations, altering operation of the infusion pump includes occluding flow through the infusion line. In some implementations, altering operation of the infusion pump includes moving an infusion pump mechanism engaged against the infusion line forward or backward to occlude flow through the infusion line.

Some embodiments of the present disclosure provide, calculating an actual rate of fluid pressure change; and altering operation of the infusion pump if the actual fluid pressure slope profile is greater than zero. In some embodiments, altering operation of the infusion pump includes moving an infusion pump mechanism of the infusion pump engaged against the infusion line forward or backward to occlude flow through the infusion line. In some implementations, altering operation of the infusion pump includes occluding flow through the infusion line.

Some implementations of the present disclosure provide, a method of detecting a defective valve in an infusion line coupled to a first fluid source and a second fluid source, the method comprising: sampling fluid pressure of the first fluid source and the second fluid source within an infusion line upstream of the infusion pump; calculating an actual fluid pressure slope profile, the fluid pressure slope profile being a change in pressure over discrete intervals; and altering operation of the infusion pump if the change in pressure of the actual fluid pressure slope profile (i) exceeds the change in pressure of an expected first fluid pressure slope profile and then (ii) does not achieve the change in pressure of an expected second fluid pressure slope profile.

In some aspects of the present disclosure, altering operation of the infusion pump includes activating an alarm. In some implementations, altering operation of the infusion pump includes occluding flow through the infusion line.

Some embodiments of the present disclosure provide, detecting a decrease in the actual fluid pressure slope profile indicating equilibrium between a head height of the first and second fluid source; and altering operation of the infusion pump if an actual volume of fluid directed through the infusion line is less than an expected volume of fluid to be directed through the infusion line. Some aspects of the present disclosure provides, positioning the second fluid source at a higher elevation than the first fluid source.

Some embodiments of the present disclosure provide, a method for controlling fluid flow through an infusion pump from a first fluid source and a second fluid source, the method comprising: sampling fluid pressure of a first fluid source and a second fluid source within an infusion line upstream of the infusion pump operating at a first fluid flow rate; calculating a fluid pressure slope profile, the fluid pressure slope profile being a change in pressure over discrete intervals; detecting equilibrium between a head height of the first and a second fluid sources; and maintaining the rate of fluid flow until the second fluid source is flushed to the infusion pump.

Some aspects of the present disclosure provide, detecting a change in pressure indicating the head height of the second fluid source within a container of the second fluid source; detecting a change in pressure indicating that the head height of the second fluid source passes through a drip chamber coupled to the second fluid source; detecting a change in pressure indicating the head height of the second fluid source passes within a tubing coupled to the second fluid source; detecting a change in pressure indicating the head height of the second fluid source is equal to the head height of the first fluid source; wherein the fluid pressure slope profile comprises a first, a second, and a third slope profile segment, and equilibrium between the first and second fluid source head heights is detected when a slope of the third slope profile segment is less than one-half of a slope of each of the preceding first slope profile segment and the preceding second slope profile segment.

Some implementation of the present disclosure provide, maintaining the rate of fluid flow until the second fluid source is flushed to the infusion pump comprises an additional volume predetermined based on known parameters of the infusion set. Some implementation of the present disclosure provide, maintaining the rate of fluid flow until the second fluid source is flushed to the infusion pump comprises an additional volume selected by a user.

Some embodiments of the present disclosure provide, a system for detecting unintentional fluid flow through an infusion line, the system comprising: an infusion pump coupled with the infusion line; a pressure sensor coupled to the infusion line upstream of the infusion pump, the pressure sensor configured to sample fluid pressure within the infusion line; a memory adapted to store the fluid pressure values; and a processor in communication with the pressure sensor and the memory, the processor configured to: calculate an actual fluid pressure slope profile; compare the actual fluid pressure slope profile with an expected fluid pressure slope profile; and alter operation of the infusion pump if a change in pressure of the actual fluid pressure slope profile exceeds, by a predetermined threshold, a coincident change in pressure of an expected fluid pressure slope profile.

Some embodiments of the present disclosure provide, a system for detecting a defective valve in an infusion line coupled to a first fluid source and a second fluid source: an infusion pump coupled with the infusion line; a pressure sensor coupled to the infusion line upstream of the infusion pump, the pressure sensor configured to sample fluid pressure within the infusion line; a memory adapted to store the fluid pressure values; and a processor in communication with the pressure sensor and the memory, the processor configured to: calculate an actual fluid pressure slope profile; compare the actual fluid pressure slope profile with an expected fluid pressure slope profile; and alter operation of the infusion pump if a change in pressure of the actual fluid pressure slope profile (i) exceeds a coincident change in pressure of an expected first fluid pressure slope profile and then (ii) does not achieve a coincident change in pressure of an expected second fluid pressure slope profile.

Some embodiments of the present disclosure provide, a system for controlling fluid flow through an infusion pump from a first fluid source and a second fluid source: the infusion pump coupled with an infusion line; a pressure sensor coupled to the infusion line upstream of the infusion pump, the pressure sensor configured to sample fluid pressure within the infusion line; a memory adapted to store the fluid pressure values; and a processor in communication with the pressure sensor and the memory, the processor configured to: calculate an actual fluid pressure slope profile; detect a decrease in a change in pressure of the fluid pressure slope profile indicating equilibrium between a head height of the first and second fluid source; and maintain a rate of fluid flow to direct all fluid from the second fluid source through the infusion line.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, values, quantities, and dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
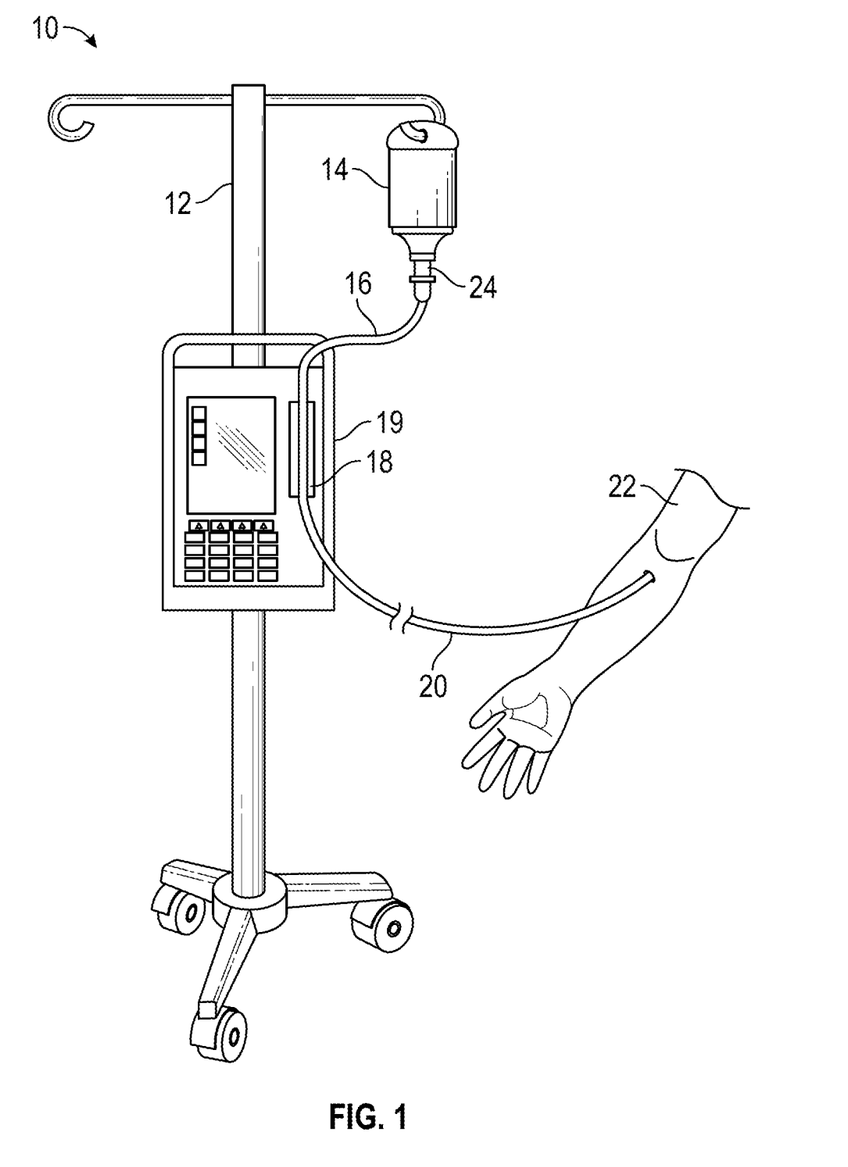
FIG. 1 illustrates an example infusion system in accordance with aspects of the present disclosure.

FIG. 1 illustrates an example infusion system 10 coupled to a patient. In particular, an infusion pump 19 is shown mounted to an intravenous (I.V.) pole 12 on which a fluid source 14 containing an I.V. fluid is held. A drip chamber 24 is coupled to an outlet of the fluid source 14, and an upstream portion of the infusion line 16 is connected to an outlet of the drip chamber 24. The upstream infusion line 16 is a conventional I.V. infusion-type tube typically used in a hospital or medical environment, and is made of any type of flexible tubing appropriate for use to infuse therapeutic fluids into a patient, such as polyvinylchloride (PVC). The upstream infusion line 16 is connected with another tube portion 18 that is flexible and is mounted in operative engagement with an infusion pump 19 having a pumping mechanism, for directing fluid through a downstream infusion line 20, for example, to a vein in the patient's arm 22. It will be understood by those skilled in the art that the upstream infusion line 16, the flexible portion infusion line 18, and the downstream infusion line 20 may be portions of a continuous length of flexible tubing, with the portions defined by the location of the infusion pump 19.

Figure 2:
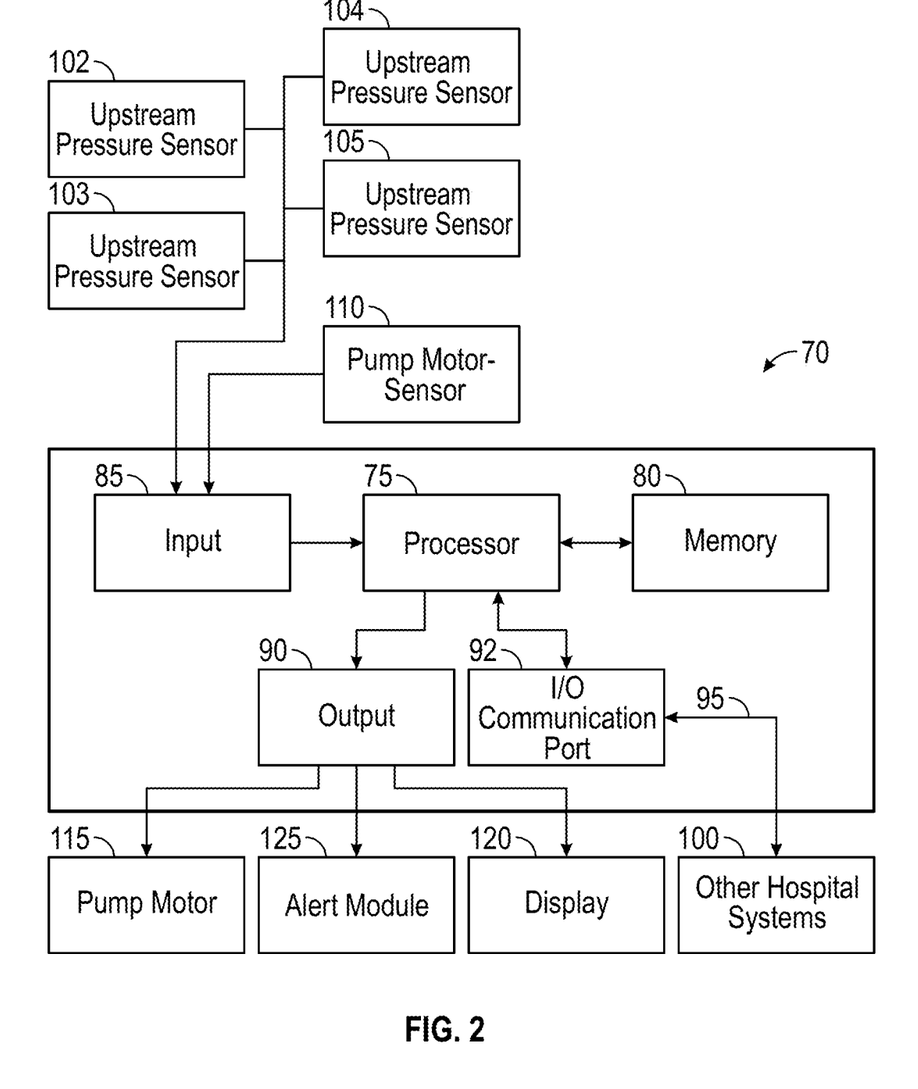
FIG. 2 illustrates a block diagram of an example infusion pump control module in accordance with aspects of the present disclosure.

Referring to FIG. 2, in some embodiments, the infusion pump includes an infusion pump control module 70 configured or programmed to control the operation of the infusion pump mechanism so that a desired amount of medication or other fluid is directed into the patient over a desired period of time. In some aspects, the infusion pump control module 70 includes a microprocessor 75, a memory 80 associated with the microprocessor 75, one or more inputs 85 for inputting signals to the microprocessor, and one or more outputs 90 for outputting signals from the microprocessor. For example, the one or more inputs may include a keyboard 102, an air detector 103, a downstream pressure sensor 104, or an upstream pressure sensor 105.

In some embodiments, the infusion pump control module 70 is in communication with other systems 100, such as a pharmacy information system, hospital administration system, or other such systems in the institution using an input/output communications port 92 and a communication means 95. The input/output communications port 92 may be any port configured to send and receive data using appropriate communication protocols, such as RS232 and the like. For example, the input/output communications port 92 may be a serial port, a parallel port, a USB, or other suitable port. It will also be understood that the input 85 and the output 90 may be combined in such a manner that all signals to and/or from the processor are communicated through one or more input/output ports 92, rather than through separate inputs and outputs.

The communication means 95 may be a hard wired or wireless connection to another computer, a local area network, a wide area network, a telephone line to a remote server or client system, or the Internet. The communication means may include specialized connection devices for connecting to optical fiber, coaxial cable, Ethernet cabling, or other communication lines. Alternatively, wireless connections may be used, which may also include the use of suitable transmitters and receivers as is known in the art. Such wireless connectivity may include use of infrared, RF, Bluetooth or Wi-Fi (IEEE 802.11b) communication means and the like. Additionally, the microprocessor 75 is commonly programmed using either embedded programming instructions or suitable software so that the microprocessor can carry out the tasks desired of it.

In some embodiments, the microprocessor 75 receives signals from an upstream pressure sensor 105 through the input 85 (typically an amplifier and A/D converter). The upstream pressure sensor 105 is disposed adjacent an upstream infusion line so as to monitor the pressure within the upstream infusion line, and provide signals representative of the sensed pressure within the infusion line to the microprocessor 75. The microprocessor 75, as described above, is programmed using appropriate software or embedded commands to analyze the signals received from the upstream pressure sensor 105. After analysis of the received upstream pressure signals is completed, the processor may output a signal through the output 90. This signal output may be directed to the pump motor 115 to control the infusion of fluid to the patient.

In some embodiments, the output signal is directed to a display 120 to inform an operator of the status of the pump and/or the pressure within the upstream infusion line. This display may also include a means of providing a visual alert, such as a flashing display, blinking light, or a change in text color on the display to alert an operator that the infusion set-up requires attention.

In some embodiments, the output signal is directed to an alert module 125. This alert module may be a separate module of the processor 75 that is controlling the infusion pump, or it may be located at a location remote from the pump, and/or associated and in communication with a separate processor remote from the pump. The alert module 125 may be configured to provide visual, auditory, or a combination of visual and auditory notifications to care givers to alert the caregiver that attention must be given to the infusion system. The alert module may produce signals that are communicated to consoles at the bed side, the nurse station, or a centrally located monitoring system. Additionally, various combinations of display changes and auditory alerts may be used to signify a priority of an alert, so that alerts that do not require immediate attention are less noticeable than alerts that require immediate attention to correct a problem before harm to the patient being infused can occur. The alert module 125, in some embodiments, may be configured to control the pump when activated. For example, the alert module 125 may control the pump to decrease pumping operation of the pump until a caregiver manually addresses the alert module 125. For example, the pumping operation may be decreased by one-third, one-half, or one-fourth of the normal pumping operation. Under some applications, for example, if it is detected a pump is not operating properly, the alert module 125 may alter the pumping operation to deviate from the normal pumping operation.

The alert module 125 may also provide signals representing the progress of the infusion, including any alerts generated due to a sensed reduced or negative pressure in the upstream infusion line 16 (FIG. 1), to a database where the information is stored for later inspection and analysis. The database may be associated with the pump, or the database may be remote from the pump. For example, where the pump is controlled by a remote controller, the database may be located and associated with the remote controller. In another embodiment, the database may be part of an institutional information system that may be part of an enterprise wide network.

In each embodiment, the microprocessor 75 is configured to receive signals from a pump motor sensor 110 through the input 85. The microprocessor 75 may monitor the function of the pump, collecting, analyzing, and storing information related to the infusion, such as, for example, the start time and completion time of the infusion, the amount of fluid infused, and the number of pump cycles that have been completed since the start of the infusion or since a selected time in the past. This information may be stored in the memory 80 for later retrieval and analysis, or the information may be communicated to another, remote, system using the communication means 95.

Figure 3A:
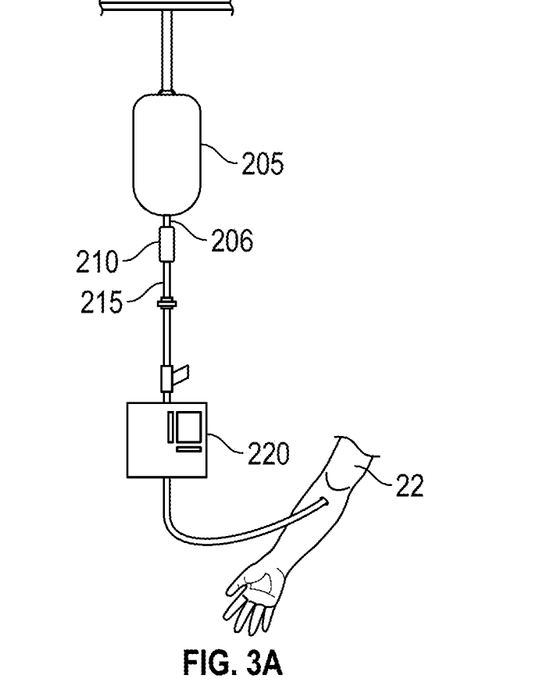
FIG. 3A illustrates an example infusion system.
Figure 3B:
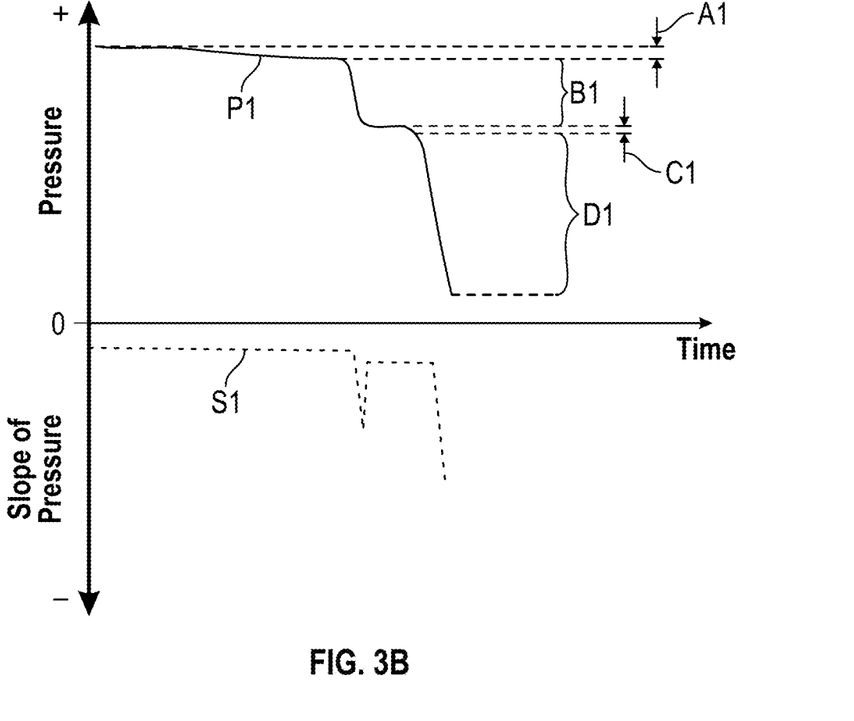
FIG. 3B illustrates a graph of fluid pressure and fluid pressure slope profiles over time in accordance with aspects of the present disclosure.

Referring to FIGS. 3A and 3B, an example of an infusion system and a design and software analysis of an embodiment of the present invention are illustrated, respectively. The infusion system includes a fluid container 205 that is filled with a fluid. A drip chamber 210 is generally located adjacent the bottom of the container 205. A length of flexible infusion line extends from the bottom of the drip chamber 210 and into an infusion pump 220. The infusion pump 220 includes an upstream pressure sensor as well as a pumping mechanism, such as a peristaltic mechanism. In some embodiments, the upstream pressure sensor is a separate component coupled to the infusion pump or infusion line.

As fluid is directed by the infusion pump 220 from the fluid source 205 and infusion line 215 to the patient 22, the level of fluid decreases or lowers. The upstream pressure sensor, in some embodiments, measures gauge or relative hydrostatic "head" pressure which is determined by the elevation of the top of the fluid level above the intake sensor. During an infusion, the processor controlling the infusion pump motor also samples the output of the upstream pressure sensor. As the fluid level in the system decreases, moving towards the infusion pump 220, the measured fluid hydrostatic pressure reduces. By sampling the fluid pressure, an algorithm detects the mean intake pressure over selected intervals such as the mechanism cycle volume. Using the averages of mean intake pressure, a rate of reduction (i.e., change) in pressure is computed as a differential. Finally, the processor records profiles of the pressure slope over at least portions of the delivery. In some aspects, the fluid pressure slope profiles represent changes in pressure over discrete intervals. The discrete intervals may be time, such that the fluid pressure slope profiles reflect change in pressure over time. In some embodiments, the discrete intervals may be volume of fluid, such that the fluid pressure slope profiles reflect change in pressure over a pumped fluid volume, preferentially the mechanism cycle volume. Under normal infusion circumstances, the fluid pressure slope profiles are represented by line S1 in the graph of FIG. 3B. The hydrostatic head pressure change due to the decreasing level of fluid within the upstream infusion line 215 is represented by line P1 in the graph of FIG. 3B. In some aspects, the fluid pressure slope profiles represent a slope by linear least square fit in water/mL, and the hydrostatic head pressure represents a revolution synchronous mean pressure in inches water.

Because the volume of fluid being withdrawn from the container 205 by the infusion pump 220, in a typical mechanism pressure sensing cycle, is small relative to the volume of fluid within the container 205, the fluid level within the container decreases or lowers relatively slowly. The change of pressure when the fluid surface level is within the container 205 is represented by segment A1 of line P1. However, when the fluid surface level reaches the cannula 206 of the drip chamber 210, which typically has much less volume than the container 205, the amount of fluid removed during each pressure sensor sampling cycle results in a relatively large change in fluid level with each sample. This rapid reduction in the level of the fluid appears as a large negative-going pressure signal, or negatively-oriented pressure signal, represented by segment B1 of line P1. The change of pressure when the fluid surface level is within the drip chamber 210 is represented by segment C1 of line P1. Once the drip chamber 210 empties, the fluid surface level enters the relatively small bore of the infusion line 215, resulting in a more rapid pressure decrease and large negative-going pressure signal, or negatively-oriented pressure signal, represented by segment D1 of line P1. The described pressure values, together with their rate of change and sequence of occurrence, form the basis by which the infusion pump of the present disclosure is capable of estimating the position of the top of the fluid at several points in its journey through the container, drip chamber and infusion line.

Under some circumstances, the infusion pump fails to control the rate of fluid flow through the system. This "unintentional fluid flow" through the infusion line causes fluid to be directed by the force of gravity to the patient 22 or out of the system and into the environment. Although a various circumstances may cause the unintentional fluid flow, several non-limiting circumstances are discussed herein. In an example, unintentional fluid flow occurs when the infusion pump 220 fails to stop fluid flow through the infusion line. The infusion pump 220 may fail to stop fluid flow through the infusion line when a pumping mechanism within the infusion pump fails to occlude the passage within the infusion line because debris or a foreign object is lodged in the tubing. In another example, unintentional fluid flow occurs when an infusion pump component is broken or missing, or the infusion line contains a hole or faulty connection to another component. It is important to detect unintentional fluid flow through an infusion line because uncontrolled fluid flow may cause fluid to be directed by the force of gravity at greater rates than therapeutically acceptable, possibly causing over-infusion and physical harm to the patient and/or loss of medication.

Figure 4:
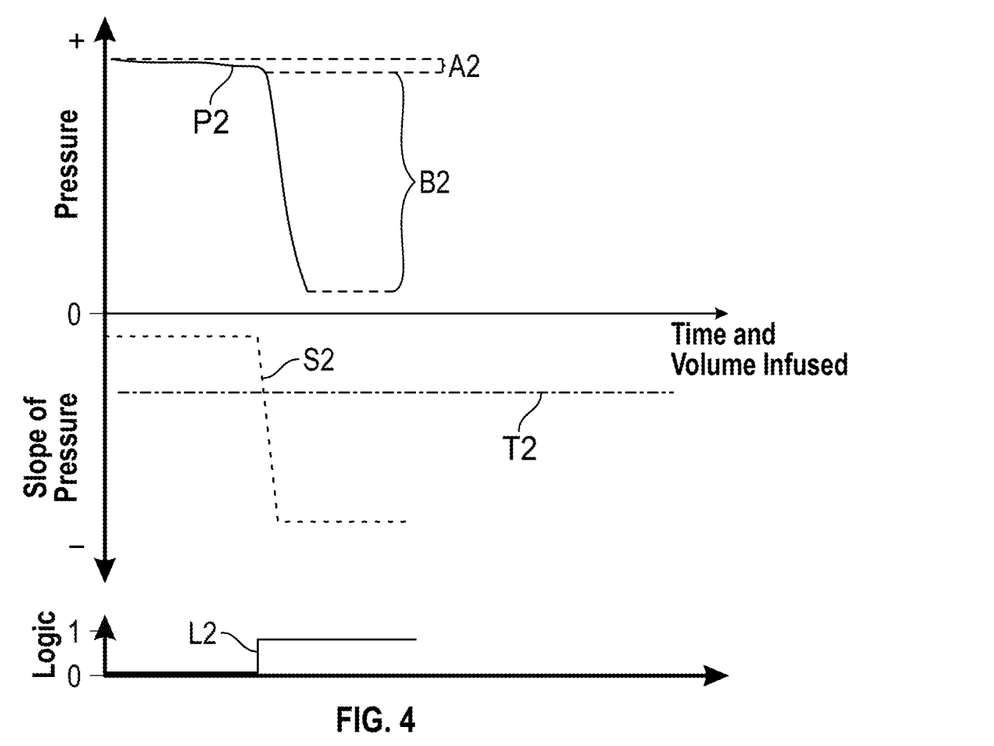
FIG. 4 illustrates an example graph of processor logic, fluid pressure, and fluid pressure slope profiles over time in accordance with aspects of the present disclosure.

Referring to FIG. 4, a graphical analysis of unintentional fluid flow through the infusion line of the system is illustrated. The graph illustrates an abnormal fluid pressure slope profile S2 and the head pressure change P2 due to the decreasing level of fluid within the upstream infusion line.

When a fluid source is coupled to the system, the fluid level within the container decreases or lowers relatively slowly. The change of pressure when the fluid surface level is within the container is represented by segment A2 of line P2. However, when unintentional fluid flow occurs, the fluid level within the system and the head pressure may decrease rapidly. An unintentional fluid flow is represented by segment B2 of line P2.

Because the infusion pump has failed to control the rate of fluid flow, the fluid pressure slope profile S2 illustrates a negative slope profile that deviates from a normal fluid pressure slope profile S1 (FIG. 3B). In some embodiments, the system detects when a negative slope profile reaches a pre-determined threshold value, represented by the line T2. This threshold may be estimated since the pump 'knows' the volume to be infused which allows an estimate of the container size and thus its cross sectional area. This cross section, together with the flow rate provides an approximation of the normal slope value. When a fluid pressure slope profile S2 exceeds the threshold value T2, the logic of the processor is programmed to alter operation of the infusion pump. Optionally, operation of the infusion pump is stopped and/or an urgent alarm activated so that the operator or a caregiver may intervene and correct the abnormal flow condition. The logic of the processor is represented by the line L2. In a non-limiting example using logic of the processor to alter operation of the infusion pump, the logic equals zero if the fluid pressure slope profile S2 is less than the threshold value T2, otherwise, logic equals zero.

In some aspects, the system compares the measured or actual fluid pressure slope profiles with expected fluid pressure slope profiles. If the change in pressure of an actual fluid pressure slope profile varies from the change in pressure of an expected fluid pressure slope profile by a predetermined threshold, the logic of the processor is programmed to alter operation of the infusion pump.

The processor may alter operation of the infusion pump in a number of ways, including for example, activating an alarm signal to a caregiver indicating that the infusion system needs attention. In some aspects, the processor may respond by occluding flow through the infusion line. For example, a mechanical brake or occluder is activated to compress the tubing of infusion line, thereby preventing fluid flow. In some aspects, the mechanical occluder is a mechanism independent of the pumping mechanism.

In some embodiments, the processor may respond by moving or rotating an infusion pump mechanism engaged against the infusion line forward or backward to occlude fluid flow through the infusion line. For example, a peristaltic pump mechanism with a first point engaged against the infusion line when unintentional fluid flow through an infusion system is detected, can be moved to engage a second point against the infusion line. By moving the mechanism, debris is permitted to be dislodged from within the infusion line.

In some embodiments, the pumping mechanism can have an intake valve and an outlet valve, with which there are certain positions within the mechanism cycle when both the intake and outlet valves are simultaneously compressed. In certain circumstances, should a spring which applies this compression fail, the effectiveness of the control of flow is reduced. However, the processor may alter operation of the infusion pump to rotate a driveshaft of the pumping mechanism to attempt to occlude one of the two valves. By occluding one of the two valves, a greater force may be applied to the infusion line to restore full control.

In some embodiments, the system confirms that occlusion of the infusion line is achieved. For example, the processor may sample the pressure and calculate a fluid pressure slope profile to determine if a slope of the fluid pressure slope profile is greater than zero over a period of time. If the slope of the fluid pressure slope profile is greater than zero over a period of time (e.g., 2 seconds, 10 seconds, 30 seconds, 1 minute, 5 minutes, etc.), there is unintentional fluid flow through an infusion system, prompting subsequent alteration of the infusion pump operation as explained above. For example, the processor may again respond by moving or rotating an infusion pump mechanism engaged against the infusion line forward or backward to occlude fluid flow through the infusion line. In this manner, the processor can test whether the pump is adequately stopping fluid through the I.V. set and find effective pump positions to increase the pump's ability to stop the fluid.

Figure 5A:
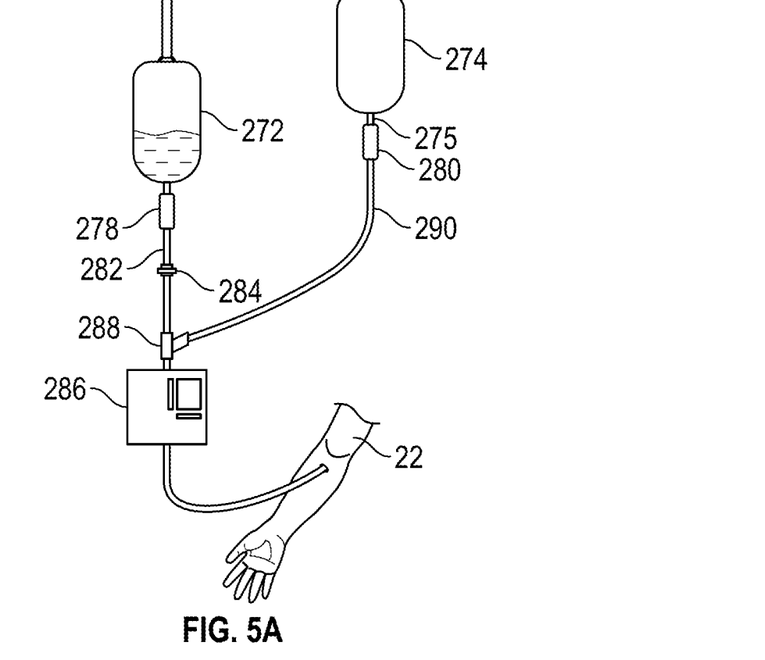
FIG. 5A illustrates an example infusion system.
Figure 5B:
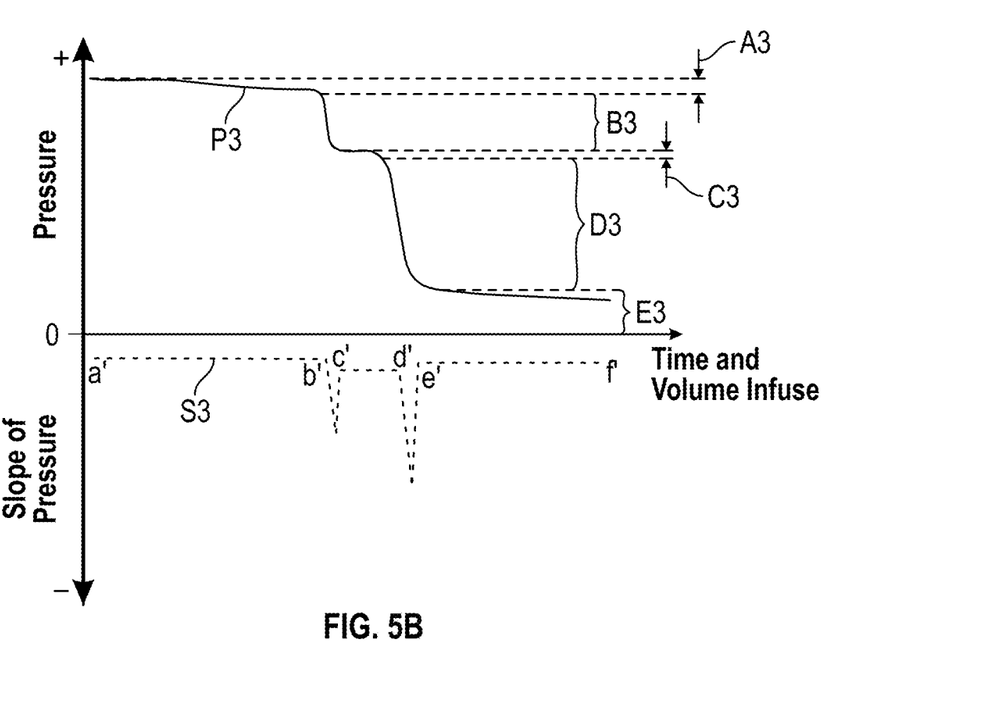
FIG. 5B illustrates a graph of fluid pressure and fluid pressure slope profiles over time in accordance with aspects of the present disclosure.

Referring to FIGS. 5A and 5B, an example of an infusion system and a design and software analysis of an embodiment of the present invention are illustrated, respectively. An example of an infusion system is illustrated with a primary fluid source container 272 and a secondary fluid source container 274 connected to an upstream infusion line to infuse a primary and/or secondary fluid to the patient 22. The primary fluid source container 272 and the secondary fluid source container 274 each include a drip chamber 278 and 280 respectively. A fitting 288, including a port, connects a secondary infusion line 290 from the secondary fluid source container 274 to the upstream infusion line. A primary infusion line 282, includes a check valve 284 and fluidly connects the primary fluid source container 272 to the fitting 288. The secondary container source container 274 is positioned higher than the primary source container 272 so that pressure from the secondary fluid will cause the check valve 284 to obstruct the flow of primary fluid toward the infusion pump 286, and direct the flow of secondary fluid toward the infusion pump 286. A pressure sensor samples the pressure in upstream infusion line.

Under normal infusion circumstances, the fluid pressure slope profiles are represented by line S3 in the graph of FIG. 5B. The head pressure change due to the decreasing level of fluid within the upstream infusion lines is represented by line P3. The portion of line P3, indicated by segment A3, represents the pressure change of secondary fluid within the secondary fluid source container 274, which is slowly decreasing as the fluid surface level in the secondary container 274 decreases. When the fluid surface level reaches the drip chamber cannula 275, the pressure change, indicated by segment B3 of line P3, decreases at a faster rate than segment A3.

When the fluid surface level reaches the drip chamber 280, the pressure change, indicated by segment C3 of line P3, decreases at a slower rate than segment B3. When the fluid surface level reaches the secondary infusion line 290, the pressure change (indicated by segment D3 of line P3) decreases at a faster rate, and for more fluid/time, than segments A3 and C3. When the level of fluid in the secondary infusion line 290 decreases to at or near the level of primary fluid in the primary fluid source container 272, the pressure against the check valve 284 is reduced such that the check valve opens, permitting the primary fluid and secondary fluid to enter upstream infusion line. When primary and secondary fluid are permitted to enter upstream infusion line, the pressure change, indicated by segment E3 of line P3, decreases at a slower rate than segments B3 and D3. Algorithmic analysis of the changes in fluid pressure slope profiles, and the sequence in which the changes occur relative to the start of infusion, form the basis by which the infusion pump of the present disclosure is capable of altering operation, including, for example, transitioning from a secondary flow rate to a primary flow rate, and/or directing a "pre-flush" or "post-flush" operation.

Under some circumstances, a defective check valve 284 in the primary infusion line permits a portion of the secondary fluid to be diverted into the primary infusion line instead of being directed entirely to the infusion pump 286. If the check valve 284 fails to obstruct the primary infusion line when a secondary fluid is coupled to the system, the secondary fluid will not be infused as intended, resulting in incomplete treatment, delayed treatment, undesired medication interaction, or missed dosage of medication among other circumstances.

Figure 6:
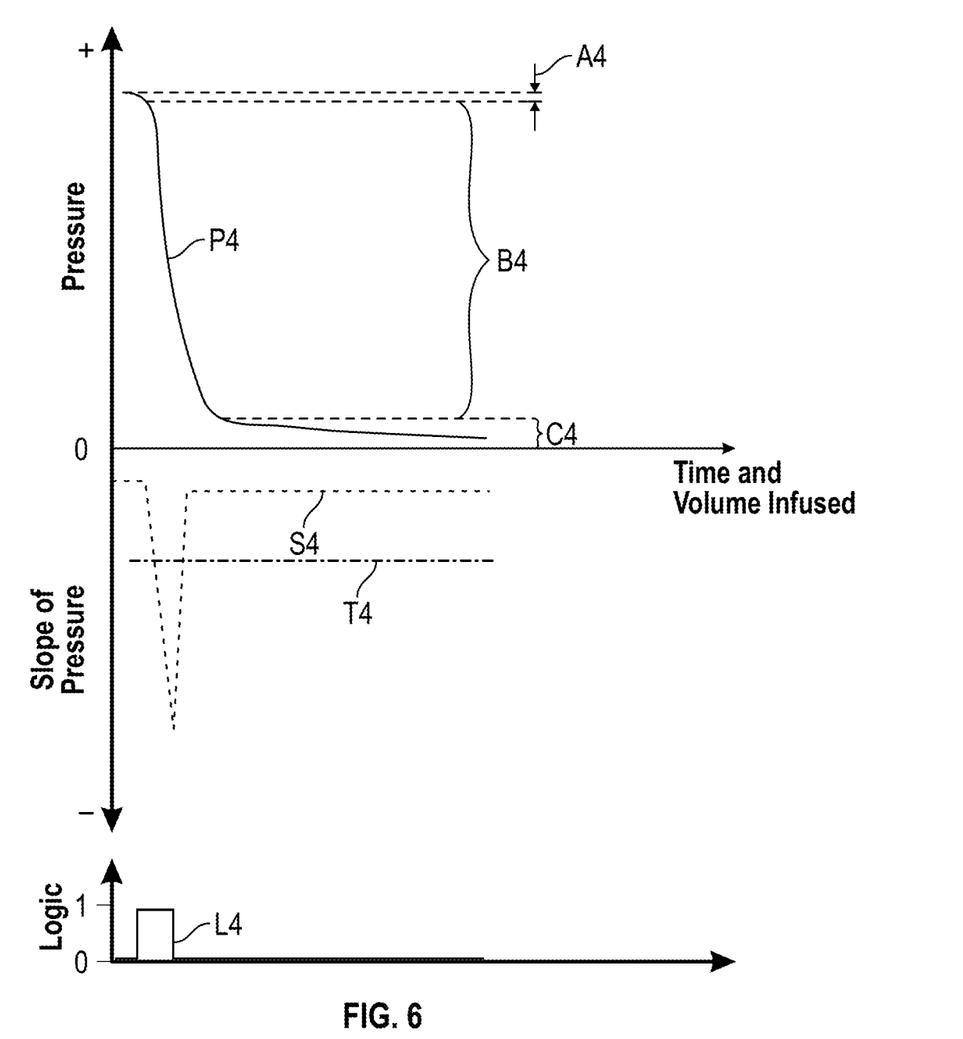
FIG. 6 illustrates an example graph of processor logic, fluid pressure, and fluid pressure slope profiles over time in accordance with aspects of the present disclosure.

Referring to FIG. 6, a graphical analysis of the fluid flow through an infusion system having a defective check valve is illustrated. The graph illustrates fluid pressure slope profiles S4 and the head pressure change P4 due to the decreasing level of fluid within the upstream infusion line. Because the check valve 284 (FIG. 5A) fails to obstruct the primary infusion line 282, the graphical analysis deviates from the graph in FIG. 5B. When a secondary fluid source is coupled to the system with the secondary fluid source container 274 positioned above the primary fluid source container 272, the secondary fluid flows toward the infusion pump 286. The change of pressure when the secondary fluid source is coupled to the system is represented by segment A4 of line P4. Because of the defective check valve 284, the secondary fluid flows rapidly past the check valve 284 into the primary infusion line 282 and the primary fluid source container 272 until an equilibrium between the level of primary and secondary fluid is reached. The decreasing secondary fluid level results in an abnormally rapid decrease in fluid pressure, thereby producing the head pressure change represented by segment B4 of line P4. When equilibrium between the level of primary and secondary fluid is reached, the head pressure change, indicated by segment C4 of line P4, decreases at a slower rate than segment B4 of line P4. The corresponding fluid pressure slope profiles are represented by line S4 of the graph in FIG. 6.

In some embodiments, the system detects when a fluid pressure slope profiles reach a pre-determined threshold value, represented by the line T4 in the graph of FIG. 6. When fluid pressure slope profiles S4 reach the threshold value, the logic of the processor is programmed to alter operation of the infusion pump. The logic of the processor is represented by line L4.

In some aspects, the system compares the measured or actual fluid pressure slope profiles with an expected first fluid pressure slope profile, and determines if the actual fluid pressure slope profile achieves an expected second fluid pressure slope profile. If the change of pressure in an actual fluid pressure slope profile exceeds the change in pressure of an expected first fluid pressure slope profile and then does not achieve the change in pressure of an expected second fluid pressure slope profile, the logic of the processor is programmed to alter operation of the infusion pump.

The processor may alter operation of the infusion pump in a number of ways, including for example, activating an alarm signal to a caregiver indicating that the infusion system needs attention. In some aspects, the processor may respond by occluding flow through the infusion line. For example, a mechanical brake or occluder is activated to compress the tubing of the infusion line to prevent fluid flow. In some aspects, the mechanical occluder is a mechanism independent of the pumping mechanism.

Under some circumstances, the infusion of a secondary fluid does not occur as intended due to incorrect determination of a fluid source container volume or inaccurate setting of the secondary volume-to-be-infused. For example, referring to the infusion system of FIG. 5A, a secondary fluid source container 274 is coupled to an upstream infusion line between a check valve 284 and an infusion pump 286. To fill, or "prime," the secondary infusion line 290 with fluid, the secondary fluid source container 274 is lowered below the primary fluid source container 272. After the secondary infusion line 290 is filled with the primary fluid, the primary and secondary fluid source containers are secured so that the primary fluid source container 274 is below the secondary fluid source container 274. With the secondary fluid source container 274 positioned higher than the primary fluid source container 272, the pressure exerted by the secondary fluid causes the check valve 284 to prevent flow of the primary fluid toward the infusion pump 286, but permits flow of the secondary fluid to the infusion pump 286.

If, during configuration of the infusion pump, the volume of fluid in the primed secondary infusion line 290, the volume of fluid in the secondary fluid source container 274, the total fluid volume-to-be-infused, the secondary fluid infusion rate, or the secondary fluid infusion time are not considered, or are incorrectly programmed, the secondary fluid will not be directed by the infusion pump as intended.

For example, a secondary infusion line 290 contains 5 mL of fluid when fully primed. The secondary fluid source 274 is nominally 50 mL with an over-fill of 4 mL and 10 mL of medication added. The total volume of priming fluid (e.g., primary fluid) in the path from the secondary fluid source 274 to the infusion pump 286 is approximately 25 mL (i.e., 5 mL in the secondary infusion line 290 and 20 mL in the upstream infusion line). If the infusion pump 286 is programmed to direct a secondary fluid volume of 50 mL in one hour followed by switching the pump to a rate of primary fluid flow (e.g., 20 mL/hr), then only the priming fluid in the path from the secondary fluid source 274 to the infusion pump 286 will be directed by the infusion pump during the first 30 minutes. During an additional 30 minutes, a portion of the total secondary fluid will be directed by the infusion pump. After the programmed one hour, the infusion pump will switch the pump to a rate of primary fluid flow (e.g., 20 mL/hr), resulting in the remaining 25 mL of secondary fluid requiring more than one hour to be direct to the patient. Therefore, 50 mL of secondary fluid that is intended to be infused to the patient in one hour will not start until 30 minutes after initiating delivery of the secondary fluid, and will then take more than one hour to deliver to the patient.

Figure 7:
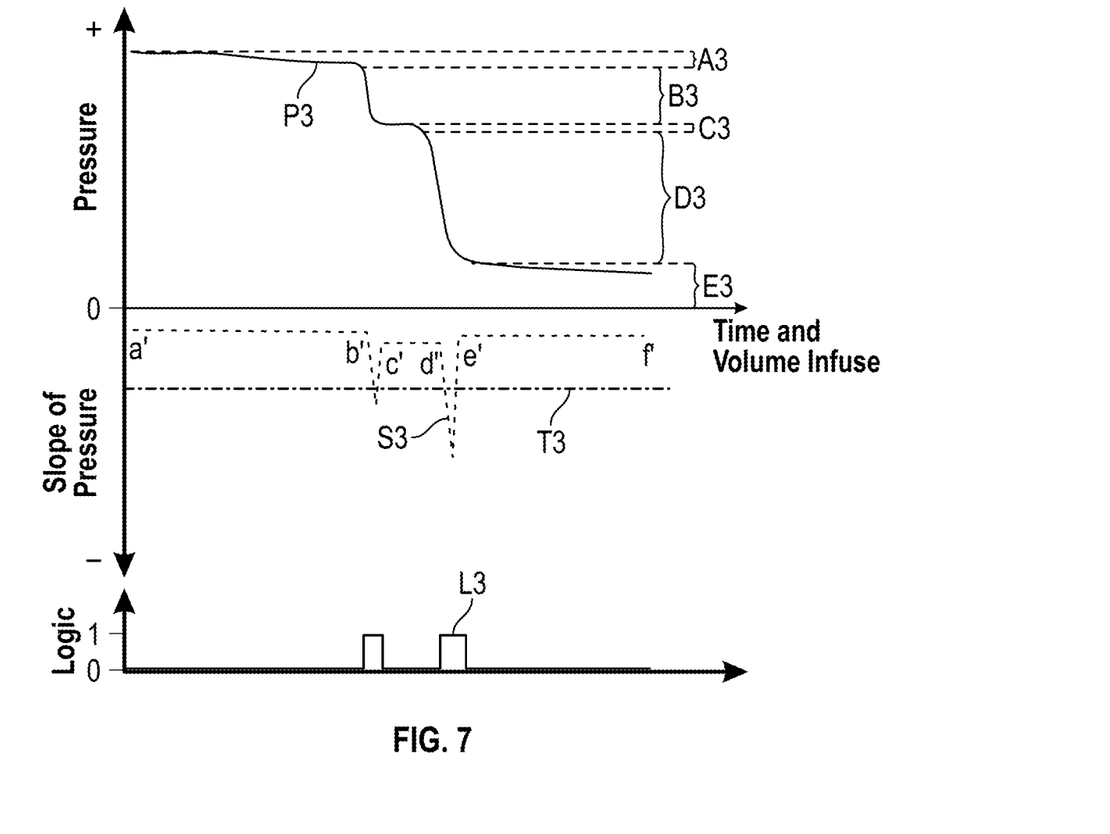
FIG. 7 illustrates an example graph of fluid pressure and fluid pressure slope profiles over time in accordance with aspects of the present disclosure.

Referring to FIG. 7, in some embodiments, fluid pressure slope profiles are utilized to detect the position of fluid within the system, thereby permitting the system to infuse the secondary fluid and primary fluid at the intended time, volume, and flow rate. The graphical analysis of FIG. 7 corresponds to a graphical analysis of the fluid flow through the system illustrated in FIG. 5A. As explained with reference to the infusion system in FIG. 5A, fluid pressure slope profiles are represented by line S3, and head pressure change due to the decreasing level of fluid upstream of the infusion pump 286 are represented by line P3. The system detects when fluid pressure slope profiles reach or pass a predetermined threshold value, represented by the line T3. When a fluid pressure slope profiles reach or exceed the threshold value, the logic of the processor, represented by the line L3, is programmed to provide an output value. For example, the logic output equals zero if the fluid pressure slope profile S3 is greater than the threshold value T3, and the logic output equals one if the fluid pressure slope profile S3 is less than the threshold value T3. In some aspects, the system detects when a fluid pressure slope profile reaches or exceeds more than one pre-determined threshold value.

Referring to FIGS. 5B and 7, an upstream pressure sensor samples the pressure of a fluid upstream of the infusion pump 286. The system calculates fluid pressure slope profiles S3 representing changes in pressure over discrete intervals due to the decreasing level of fluid within the upstream infusion lines. The calculated, or actual, fluid pressure slope profiles S3 indicate the fluid surface level within the system, including equilibrium between the primary and secondary fluid surface level. When equilibrium is reached, fluid is drawn from the primary infusion line 282 and the secondary infusion line 290 toward the infusion pump 286.

In some embodiments, the system detects equilibrium between the primary and secondary fluid surface level when the level of fluid in the secondary infusion line 290 is equal to the level of fluid in the primary fluid source container 272. In some aspects, equilibrium between the primary and secondary fluid surface level is detected by two strong negative slopes, segments b'-c' and d'-e' of line S3, followed by a near zero slope, segment e' to f' of line S3. The first negative slope corresponds to the fluid surface level in the drip chamber cannula 275 (segment B3 of line P3), the second negative slope corresponds to the fluid surface level in the secondary infusion line 290 (segment B3 of line P3). In some embodiments, after detecting equilibrium, the system maintains the rate of fluid flow until the secondary fluid is flushed to the infusion pump 286.

In some embodiments, the system directs fluid at a "pre-flush" flow rate when infusion of the secondary fluid is initiated. The system directs fluid at the pre-flush flow rate to transfer the priming fluid from the secondary infusion line 290 to the infusion pump 286. In some aspects, the pre-flush flow rate is higher than the rate of secondary fluid flow. After directing the priming fluid from the secondary infusion line 290, the system directs fluid at the programmed rate of secondary fluid flow.

In some embodiments, the system directs fluid at the "post-flush" flow rate after detecting equilibrium between the primary and secondary fluid surface level. The system directs fluid at the post-flush flow rate after detecting equilibrium to transfer the remaining secondary fluid from the secondary infusion line 290 to the infusion pump 286 before switching to direct fluid and the rate of primary fluid flow. In some aspects, the post-flush flow rate is higher than the rate of primary fluid flow. In some aspects, the post-flush flow rate is higher than the rate of primary fluid flow and the rate of secondary fluid flow. In some aspects, the post-flush flow rate and pre-flush flow rate are equal.

In some aspects, the system prompts a caregiver to indicate if the transfer of fluid at the pre-flush rate is to occur when infusion of the secondary fluid is initiated. In some aspects, the system prompts a caregiver to indicate if the transfer of fluid at the post-flush rate is to occur after detecting equilibrium between the primary and secondary fluid surface level. In some embodiments, the post-flush and pre-flush flow rate of preprogrammed into the system, or selected by a caregiver. In some embodiments, the system prompts a caregiver to indicate the length of time or volume of fluid for the post-flush and/or pre-flush flow rate.

It is understood that any specific order or hierarchy of blocks in the processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A method of detecting unintentional fluid flow through an infusion line, the method comprising:
    detecting measurements of fluid pressure within the infusion line upstream of an infusion pump;
    calculating a fluid pressure slope profile based at least in part on the detected fluid pressure measurements, the fluid pressure slope profile indicating a change in the fluid pressure over discrete intervals;
    prior to compressing intake and outlet valves of the infusion pump, determining that the change in the fluid pressure varies from a coincident change in pressure of an expected fluid slope profile by a threshold amount; and
    altering operation of the infusion pump.

2. The method of claim 1, further comprising detecting a failure of the compression of at least one of the intake valve or the outlet valve, and wherein said altering is performed in response to detecting the failure.

3. The method of claim 2, wherein altering operation of the infusion pump includes rotating a driveshaft of the infusion pump to occlude at least one of the intake valve or the outlet valve.

4. The method of claim 1, wherein altering operation of the infusion pump includes activating an alarm.

5. The method of claim 1, wherein altering operation of the infusion pump includes occluding flow of a fluid through the infusion line.

6. The method of claim 1, wherein altering operation of the infusion pump includes moving an infusion pump mechanism engaged against the infusion line forward or backward to occlude flow of a fluid through the infusion line.

7. The method of claim 6, further comprising:
calculating a new fluid pressure slope profile after occluding flow of the fluid through the infusion line; and
further altering operation of the infusion pump if the new fluid pressure slope profile is greater than zero.

8. The method of claim 7, wherein further altering operation of the infusion pump includes moving the infusion pump mechanism of the infusion pump engaged against the infusion line forward or backward to occlude flow of the fluid through the infusion line.

9. The method of claim 7, wherein further altering operation of the infusion pump includes occluding flow of the fluid through the infusion line.

10. The method of claim 1, further comprising:
detecting a decrease in the fluid pressure slope profile indicating equilibrium between a head height of first and second fluid sources; and
altering operation of the infusion pump when a volume of fluid directed through the infusion line is less than a volume of fluid expected to be directed through the infusion line.

11. The method of claim 1, wherein the discrete intervals correspond to volume of fluid, wherein the fluid pressure slope profile reflects change in pressure over a pumped fluid volume.

12. The method of claim 1, wherein the threshold amount is determined based on a fluid volume to be infused.

13. The method of claim 12, further comprising:
estimating a fluid container size based on the volume to be infused;
determining a cross-sectional area of the estimated container size; and
determining the threshold amount as an approximated normal slope value based on the cross-sectional area and a fluid flow rate through the infusion line.

14. A system for detecting unintentional fluid flow through an infusion line, the system comprising:
an infusion pump coupled with the infusion line, the infusion pump comprising an intake valve and an outlet valve;
a pressure sensor coupled to the infusion line upstream of the infusion pump, the pressure sensor configured to sample fluid pressure within the infusion line;
a memory adapted to store fluid pressure values; and
a processor in communication with the pressure sensor and the memory, the processor configured to:
calculate an actual fluid pressure slope profile;
compare the actual fluid pressure slope profile with an expected fluid pressure slope profile when both intake and outlet valves of the infusion pump are to be simultaneously compressed; and
alter operation of the infusion pump if a change in pressure of the actual fluid pressure slope profile varies from a coincident change in pressure of an expected fluid pressure slope profile by a predetermined threshold.

15. The system of claim 14, the processor further configured to detect a failure of compression of at least one of the intake valve or the outlet valve, wherein said altering the operation of the infusion pump is performed in response to detecting the failure.

16. The system of claim 14, wherein the infusion pump further comprises a driveshaft, and wherein said altering the operation of the infusion pump comprises rotating the driveshaft to occlude one of the intake and outlet valves.

17. The system of claim 14, further comprising an infusion pump mechanism engaged against the infusion line, wherein said altering the operation of the infusion pump includes moving the infusion pump mechanism forward or backward to occlude flow of a fluid through the infusion line.

18. The system of claim 14, further comprising an alarm, wherein said altering operation of the infusion pump includes activating the alarm.

19. The system of claim 14, the processor further configured to:
detect a decrease in the actual fluid pressure slope profile indicating equilibrium between a head height of first and second fluid sources; and
alter operation of the infusion pump when a volume of fluid directed through the infusion line is less than a volume of fluid expected to be directed through the infusion line.

20. The system of claim 14, the processor further configured to:
estimate a fluid container size based on a fluid volume to be infused;
determine a cross-sectional area of the estimated container size; and
determine the threshold as an approximated normal slope value based on the cross-sectional area and a fluid flow rate through the infusion line.

* * * * *